United States Patent [19]

Manzer et al.

[11] Patent Number: 4,944,846
[45] Date of Patent: Jul. 31, 1990

[54] PROCESS FOR THE SEPARATION OF HF VIA AZEOTROPIC DISTILLATION

[75] Inventors: Leo E. Manzer; V. N. Mallikarjuna Rao, both of Wilmington, Del.; Richard T. Rockwell; Michael A. Sisk, both of Corpus Christi, Tex.; Edwin J. Warwas, Wilmington; Roy Winteringham, Hockessin, both of Del.

[73] Assignee: E. I. DuPont de Nemours and Company, Wilmington, Del.

[21] Appl. No.: 226,737

[22] Filed: Aug. 1, 1988

[51] Int. Cl.$^5$ .................... B01D 3/00; C07C 17/00
[52] U.S. Cl. ........................... 203/1; 203/91; 203/DIG. 18; 570/168; 570/178
[58] Field of Search ............ 203/DIG. 18, 91; 570/168, 178

[56] References Cited

U.S. PATENT DOCUMENTS

| | | | |
|---|---|---|---|
| 2,406,794 | 9/1946 | Benning et al. | 570/178 |
| 2,425,752 | 8/1947 | McKenna et al. | 203/39 |
| 2,450,414 | 10/1948 | Benning | 203/80 |
| 2,450,415 | 10/1948 | Benning | 203/78 |
| 2,478,362 | 8/1949 | Benning | 203/80 |
| 2,549,609 | 4/1951 | Johnson | 570/178 |
| 3,101,304 | 8/1963 | Wiist | 570/178 |
| 3,152,051 | 10/1964 | Fainberg et al. | 570/178 |
| 3,406,099 | 10/1968 | Buckman et al. | 570/178 |
| 3,686,082 | 8/1972 | Ruehlen | 570/178 |
| 3,873,629 | 3/1975 | Jones | 570/177 |
| 3,947,558 | 3/1976 | van Eijl | 428/483 |
| 3,976,447 | 8/1976 | Merchant et al. | 55/71 |
| 4,209,470 | 6/1980 | Lorquet | 570/188 |
| 4,605,798 | 8/1986 | Abel et al. | 570/168 |
| 4,766,258 | 8/1988 | Komalsci | 570/168 |
| 4,766,259 | 8/1988 | Manzer et al. | 570/178 |

FOREIGN PATENT DOCUMENTS 0729160 3/1966 Canada ................... 203/39
0098341 1/1984 European Pat. Off. .

*Primary Examiner*—Virginia Manoharan

[57] ABSTRACT

Process for the separation of hydrogen fluoride (HF), 2,2-dichloro-1,1,1-trifluoroethane (FC-123), and/or 2-chloro-1,1,1,2-tetrafluoroethane (FC-124) from mixtures containing them by controlling the molar ratio of HF/FC-123 in the mixture prior to subjecting the mixture to azeotropic distillation.

6 Claims, 1 Drawing Sheet

PROCESS FOR THE SEPARATION OF HF VIA AZEOTROPIC DISTILLATION

FIELD OF INVENTION

Process for the separation of hydrogen fluoride (HF), 2,2-dichloro-1,1,1-trifluoroethane (FC-123), and/or 2-chloro-1,1,1,2-tetrafluoroethane (FC-124) from mixtures comprising them by azeotropic distillation.

BACKGROUND OF THE INVENTION

The efficient utilization of HF is important from both economic and process operability viewpoints. Techniques to effect the separation and recovery of HF from fluorocarbon process streams have been disclosed.

U.S. Pat. No. 2,450,415 discloses the use of a continuous separation zone to separate an organic phase from HF and then recycling the latter to the reactor feed system.

U.S. Pat No. 3,406,099 discloses an azeotropic system useful for separation of $CF_3COCF_3$, HF or $CCl_2FCClF_2$ from mixtures containing one or more of these materials.

U.S. Pat. No. 3,873,629 discloses a continuous process for separating mixtures of HF and $ClCHF_2$ by countercurrent contact of a gaseous mixture of the two components with $H_2SO_4$.

U.S. Pat. No. 3,947,558 discloses a process for the separation of HF from the reaction products generated by fluorinating a 1-3 carbon chlorinated hydrocarbon by first separating HCl, followed by cooling to form an HF-rich layer and a substantially HCl-free organic layer. This latter layer is mixed with a liquid 2 to 8 carbon glycol; after which an HF enriched glycol layer is separated from the halocarbon layer. HF is recovered from the glycol by distillation.

U.S. Pat. No. 3,976,447 discloses the separation of HF from gaseous mixtures by treatment with dry particles of $CaCl_2$, $BaCl_2$, or $SrCl_2$, after which the HF is desorbed.

U.S. Pat. No. 4,209,470 discloses a process for the separation of HF from its liquid mixtures with 1-chloro-1,1-difluoroethane by adding an auxiliary solvent to enhance the HF composition of a liquid inorganic phase in a decanter. The HF is then separated from the inorganic phase by distillation.

EP 98,341 discloses a process for the separation of HF and 1-chloro-1,1-difluoroethane which does not require an auxiliary solvent even though the feed stream to the decanter contains pentafluorobutane which the disclosure states should contribute to the mutual solubility of HF and 1-chloro-1,1-difluoroethane; and therefore, should hinder a phase separation process. The separation is done without the use of auxiliary solvents by avoiding contamination and exercising good temperature control.

The need to produce alternate fluorocarbons useful as refrigerants and blowing agents or as intermediates in the production of other fluorocarbons useful as refrigerants and blowing agents has spurred an interest in processes for the preparation of FC-123 and FC-124. These are useful themselves as blowing agents, refrigerants and intermediates in the preparation of 1,1,1,2-tetrafluoroethane (FC-134a), a highly useful fluorocarbon refrigerant.

One process for the preparation of FC-123 and FC-124, described in commonly assigned application Ser. No. 070,826, filed July 7, 1987,now U.S. Pat. No. 4,766,260 involves vapor phase hydrofluorination of halogenated alkenes with excess HF. This process produces a reaction mixture effluent consisting essentially of HF, FC-123, FC-124, tetrachloroethylene, HCl, and minor (less than 5 mole percent) amounts of other halogenated products such as 1,2,2-trichloro-1,1-difluoroethane (FC-122) and pentafluoroethane (FC-125). To maximize process efficiency it is desirable to recycle HF, FC-122, tetrachloroethylene, and a portion of the FC-123 to the synthesis reactor. It is particularly desirable to separate excess HF from the organic components of the reaction mixture effluent. This invention provides for a mechanism to accomplish this by controlling the ratio of HF/FC-123 in the mixture followed by azeotropic distillation.

SUMMARY OF THE INVENTION

The present invention provides a process for the separation of hydrogen fluoride (HF), 2,2-dichloro-1,1,1-trifluoroethane (FC-123), and/or 2-chloro-1,1,1,2-tetrafluoroethane (FC-124) from an initial mixture comprising HF, FC-123 and, optionally, FC-124 by (1) ensuring that the molar ratio of HF/FC-123 in the initial mixture is less than or equal to 1.3, (2) passing the mixture of (1) through a distillation column to form a mixture of low-boiling azeotropes comprising substantially all the HF and all the FC-124 in the initial mixture (3) removing the mixture of azeotropes from the top of the distillation column while the bottom of the distillation column is maintained at sufficient temperature and pressure, preferably by removal of FC-123, substantially free of HF, from the bottom of the distillation column.

The mixture of low-boiling azeotropes formed in accordance with this invention consists essentially of an azeotrope of HF and FC-123 and, optionally, an azeotrope of HF and FC-124. A portion of the mixture of azeotropes may be in the form of a ternary azeotrope.

DETAILS OF THE INVENTION

Figure 1:
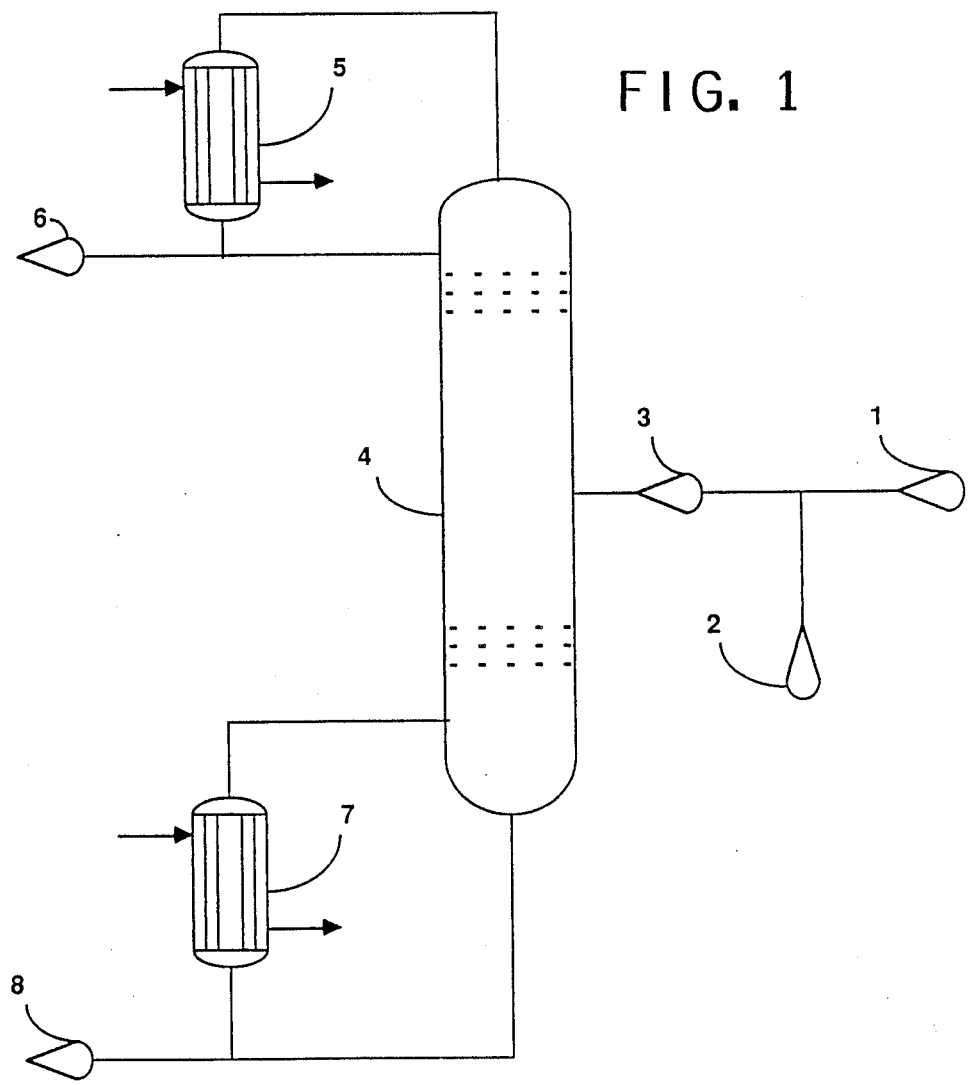
FIG. 1 is a schematic flow diagram of the process of the invention.

While the initial mixture treated in accordance with the instant invention can be obtained from a variety of sources, an advantageous use of the instant invention resides in treating the effluent mixture from the preparation of FC-123 and FC-124 by reaction of tetrachloroethylene with excess HF, so that products from the reaction can be withdrawn or recycled as desired. The effluent mixture from this reaction generally consists essentially of HF, FC-123, FC-124, tetrachloroethylene, HCl, and minor amounts, i.e., less than 5 mole %, of other halogenated products, such as 1,2,2-trichloro-1,1,difluoroethane (FC-122) and pentafluoroethane (FC-125). Generally the reaction effuents have a molar ratio of HF/FC-123 from about 0.5/1 to 20/1, and, most commonly at least 1.5/1. Consequently, in most cases FC-123 is added to reaction effluent to bring the HF/FC-123 molar ratio to 1.3/1 or less. The preferred HF/FC-123 molar ratio is from 0.8/1 to 1.3/1 to achieve maximum benefit from the instant process.

When the initial mixture treated in accordance with the invention also contains HCl and/or tetrachloroethylene, the HCl can be removed from the top of the distillation column and the tetrachloroethylene can be removed from the bottom of the distillation column.

Minor amounts of other halogenated products which may also be present in the mixture can be removed from either the top or the bottom of the distillation column depending upon their boiling points. The FC-123 is recoverable from the bottom of the column and higher boiling components are recyclable to the fluorination reaction, if desired. In practice, the mixture of low-boiling azeotropes will contain a portion of the initial FC-123 content and substantially all of the initial FC-124 content, if present. The mixture of low-boiling azeotropes will also contain substantially all of the HF and all of the FC-125 content, if present, of the initial mixture.

Applicants have found that azeotropes are formed at a variety of temperatures and pressures. At 2.50 MPa pressure and 122.6° C. applicants calculated that HF and FC-123 form an azeotrope consisting essentially of 42.4 mole percent (84.9 weight percent) FC-123 and 57.6 mole percent (15.1 weight percent) HF. At 2.50 MPa and 95.7° C. applicants calculated that HF and FC-124 form an azeotrope consisting essentially of 70.6 mole percent (94.2 weight percent) FC-124 and 29.4 mole percent (5.8 weight percent) HF. Azeotropes can range in composition from about 38.9 mole percent (83.0 weight percent) FC-123 and 61.1 mole percent (17.0 weight percent) HF at about 5° C. and about 0.10 MPa, to about 42.7 mole percent (85.1 weight percent) FC-123 and 57.3 mole percent (14.9 weight percent) HF at about 150° C. and 4.0 MPa, for one azeotrope, and from about 76.8 mole percent (95.8 weight percent) FC-124 and about 23.2 mole percent (4.2 weight percent) of HF at about −17° C. and about 0.10 MPa, to about 69.9 mole percent (94.1 weight percent) FC-124 and about 30.1 mole percent (5.9 weight percent) HF at about 122° C. and 4.0 MPa, for another azeotrope.

Applicants have discovered that azeotropic distillation of a feed mixture may be accomplished in accordance with their invention by careful control of the ratio of HF/FC-123 in the feed mixture and by control of the distillation column temperature via withdrawal of FC-123 from the bottom of the distillation column. Sufficient FC-123 is removed from the bottom of the distillation column to maintain a temperature preferably from about 50° C. to about 300° C. and a pressure from about 0.10 MPa to about 4.0 MPa at the bottom of the distillation column.

FIG. 1 is illustrative of one method of practicing this invention. Referring to FIG. 1, a feed mixture 1 is passed directly to a multiple plate distillation column 4, providing the HF/FC-123 molar ratio in the feed mixture is less than about 1.3/1. Generally reaction effluents exhibit a molar ratio of HF/FC-123 from 0.5/1 to about 20/1 and most commonly well above 1.5/1. If the molar ratio of HF/FC-123 is greater than about 1.3/1, additional FC-123 2 is fed to the feed mixture 1 to form column feed 3 having an HF/FC-123 molar ratio between about 0.8/1 and about 1.3/1 which is then passed to the multiple plate distillation column 4, which should be maintained at a bottom temperature from about 50° C. to about 300° C., and more preferably from 125° C. to 210° C., and a pressure from about 0.10 MPa to about 4.0 MPa, and more preferably from 1.5 MPa to 2.5 MPa. When tetrachloroethylene is present in the feed mixture 1, a bottom temperature of 125° C. to 210° C. and a pressure of 1.5 MPa to 2.5 MPa are preferred. Azeotropes of HF and FC-123, and of HF and FC-124 as well as HCl and trace amounts of halogenated products, such as FC-125, are removed from the top of the column 4 at from about 0° C. to about 150° C., preferably 75° C. to 125° C. and at from about 0.10 MPa to 4.0 MPa, preferably 1.5 MPa to 2.5 MPa, and passed to condenser 5 where they can be recovered as products 6 or recycled as desired. Tetrachloroethylene, any FC-123 not taken overhead in azeotrope formation, and minor amounts of halogenated products such as FC-122 exit the bottom of the column 4. Reboiler 7 provides heat input to the column by revaporizing a portion of mixture 8, which mixture can most advantageously be recycled to a synthesis reactor. The amount of FC-123 removed from the bottom of the distillation column 4 determines the temperature of the exit stream at a given operating pressure. Consequently sufficient FC-123 can be withdrawn from the bottom of the distillation column to maintain a preferred column temperature range.

EXAMPLES

In the following illustrative examples, all values for the compounds are in moles, temperatures are in Celsius. The data were obtained by calculation using measured and calculated thermodynamic properties. The numbers at the top of the columns refer to FIG. 1.

EXAMPLES 1 AND 2

The effect of the addition of more FC-123 to the distillation feed when the HF/FC-123 molar ratio exceeds 1.3/1 is shown in Table 1 for Example 1 and Table 2 for Example 2. In Example 1, the initial molar ratio of HF/FC-123 is 3.13/1 and is adjusted to 1.14/1 by FC-123 addition. In Example 2, the initial molar ratio of HF/FC-123 is 2.08/1 and is adjusted to 0.83/1 by FC-123 addition. Examination of the results show that at a bottoms temperature of about 200° C. all of the HF is removed in the top products and the tetrachloroethylene, that is removed from the bottom of the column, is free of HF and can be recycled to the reactor.

TABLE 1

| Compound | 1 Feed Mixture | 2 Addtl. FC-123 | 6 Top Products | 8 Bottom Products |
|---|---|---|---|---|
| TCE* | 12.84 | | 0.00 | 12.84 |
| HF | 53.76 | | 53.76 | 0.00 |
| FC-122 | 0.29 | | 0.00 | 0.29 |
| FC-123 | 17.16 | 30.02 | 43.20 | 3.99 |
| FC-124 | 2.55 | | 2.55 | 0.00 |
| FC-125 | 0.13 | | 0.13 | 0.00 |
| HCl | 13.27 | | 13.27 | 0.00 |
| Temp °C. | 115 | 115 | 103 | 206 |
| Press. MPa | 1.89 | 1.89 | 1.89 | 1.89 |

*Tetrachloroethylene

TABLE 2

| Compound | 1 Feed Mixture | 2 Addtl. FC-123 | 6 Top Products | 8 Bottom Products |
|---|---|---|---|---|
| TCE | 15.67 | | 0.00 | 15.67 |
| HF | 43.57 | | 43.57 | 0.00 |
| FC-122 | 0.36 | | 0.00 | 0.36 |
| FC-123 | 20.93 | 31.42 | 47.22 | 5.14 |
| FC-124 | 3.12 | | 3.12 | 0.00 |
| FC-125 | 0.16 | | 0.16 | 0.00 |
| HCl | 16.19 | | 16.19 | 0.00 |
| Temp °C. | 115 | 115 | 105 | 204 |
| Press. MPa | 1.89 | 1.89 | 1.89 | 1.89 |

COMPARATIVE EXAMPLES 1C and 2C

Table 1C for comparative Example 1C and Table 2C for comparative Example 2C show that if no additional FC-123 is added to the feed mixtures of Examples 1 and 2 then considerable amounts of HF are found in the bottom products (8, FIG. 1). In Example 1C the HF/FC-123 molar ratio is 3.13/1 and in Example 2C the molar ratio of HF/FC-123 is 2.08/1.

TABLE 1C

| Compound | 1 Feed Mixture | 2 Addtl. FC-123 | 6 Top Products | 8 Bottom Products |
|---|---|---|---|---|
| TCE | 12.84 | | 0.00 | 12.84 |
| HF | 53.77 | | 47.91 | 5.86 |
| FC-122 | 0.29 | | 0.29 | 0.00 |
| FC-123 | 17.15 | 0.00 | 17.15 | 0.00 |
| FC-124 | 2.55 | | 2.55 | 0.00 |
| FC-125 | 0.13 | | 0.13 | 0.00 |
| HCl | 13.27 | | 13.27 | 0.00 |
| Temp °C. | 115 | | 108 | 195 |
| Press. MPa | 1.89 | | 1.89 | 1.89 |

TABLE 2C

| Compound | 1 Feed Mixture | 2 Addtl. FC-123 | 6 Top Products | 8 Bottom Products |
|---|---|---|---|---|
| TCE | 15.67 | | 0.00 | 15.67 |
| HF | 43.57 | | 36.40 | 7.17 |
| FC-122 | 0.36 | | 0.36 | 0.00 |
| FC-123 | 20.93 | 0.00 | 20.93 | 0.00 |
| FC-124 | 3.12 | | 3.12 | 0.00 |
| FC-125 | 0.16 | | 0.16 | 0.00 |
| HCl | 16.19 | | 16.19 | 0.00 |
| Temp °C. | 115 | | 99 | 196 |
| Press. MPa | 1.89 | | 1.89 | 1.89 |

EXAMPLES 3 and 4

The separation by distillation is also effective when the column pressure is either 0.10 MPa or 3.55 MPa as is shown in Tables 3 and 4.

TABLE 3

| Compound | 1 Feed Mixture | 2 Addtl. FC-123 | 6 Top Products | 8 Bottom Products |
|---|---|---|---|---|
| TCE | 12.84 | | 0.00 | 12.84 |
| HF | 53.76 | | 53.76 | 0.00 |
| FC-122 | 0.29 | | 0.00 | 0.29 |
| FC-123 | 17.16 | 30.02 | 43.05 | 4.14 |
| FC-124 | 2.55 | | 2.55 | 0.00 |
| FC-125 | 0.13 | | 0.13 | 0.00 |
| HCl | 13.27 | | 13.27 | 0.00 |
| Temp °C. | 115 | 115 | 5 | 69 |
| Press. MPa | 0.10 | 0.10 | 0.10 | 0.10 |

TABLE 4

| Compound | 1 Feed Mixture | 2 Addtl. FC-123 | 6 Top Products | 8 Bottom Products |
|---|---|---|---|---|
| TCE | 12.84 | | 0.00 | 12.84 |
| HF | 53.76 | | 53.76 | 0.00 |
| FC-122 | 0.29 | | 0.00 | 0.29 |
| FC-123 | 17.16 | 30.02 | 43.20 | 3.99 |
| FC-124 | 2.55 | | 2.55 | 0.00 |
| FC-125 | 0.13 | | 0.13 | 0.00 |
| HCl | 13.27 | | 13.27 | 0.00 |
| Temp °C. | 115 | 115 | 136 | 250 |
| Press. MPa | 3.55 | 3.55 | 3.55 | 3.55 |

EXAMPLE 5

When the ratio of HF/FC-123 exiting the reactor is less than 1.3/1, i.e. 1.03/1, no additional FC-123 needs to be added to the column feed to effect separation. This is shown in Table 5.

TABLE 5

| Compound | 1 Feed Mixture | 2 Addtl. FC-123 | 6 Top Products | 8 Bottom Products |
|---|---|---|---|---|
| TCE | 20.09 | | 0.00 | 20.09 |
| HF | 27.60 | | 27.60 | 0.00 |
| FC-122 | 0.46 | | 0.00 | 0.46 |
| FC-123 | 26.88 | 0.00 | 19.64 | 7.24 |
| FC-124 | 4.00 | | 4.00 | 0.00 |
| FC-125 | 0.20 | | 0.20 | 0.00 |
| HCl | 20.77 | | 20.77 | 0.00 |
| Temp °C. | 115 | | 92 | 201 |
| Press. MPa | 1.89 | | 1.89 | 1.89 |

What is claimed:

1. A process for the separation of hydrogen fluoride from an initial mixture which comprises hydrogen fluoride and either 2,2-dichloro-1,1,1-trifluoroethane or both 2,2-dichloro-1,1,1-trifluoroethane and 2-chloro-1,1,1,2-tetrafluoroethane, comprising the steps of:

(a) controlling the molar ratio of hydrogen fluoride to 2,2-dichloro-1,1,1-trifluoroethane in said initial mixture by adding 2,2-dichloro-1,1,1-trifluoroethane when the molar ratio of hydrogen fluoride to 2,2-dichloro-1,1,1-trifluoroethane is greater than about 1.3:1, thereby providing said initial mixture with a molar ratio of hydrogen fluoride to 2,2-dichloro-1,1,1-trifluoroethane of 1.3:1, or less;

(b) separating the initial mixture provided in step (a) by azeotropic distillation in a distillation column having a temperature of from about 50° C. to 300° C. and a pressure of from about 0.10 MPa to about 4.0 MPa at the bottom of the column;

(c) removing top products from the distillation column which contain a portion of the 2,2-dichloro-1,1,1-trifluoroethane from the initial mixture provided in step (a) and substantially all of the hydrogen fluoride from the initial mixture provided in step (a) and which comprise at least one low-boiling azeotrope selected from the group consisting of azeotropes of hydrogen fluoride and 2,2-dichloro-1,1,1-trifluoroethane, azeotropes of hydrogen fluoride and 2-chloro-1,1,1,2-tetrafluoroethane, and azeotropes of hydrogen fluoride and both 2,2-dichloro-1,1,1-trifluoroethane and 2-chloro-1,1,1,2-tetrafluoroethane; and (d) removing bottom products from the distillation column which are substantially free of hydrogen fluoride and which comprise 2,2-dichloro-1,1,1-trifluoroethane; wherein sufficient 2,2-dichloro-1,1,1-trifluoroethane is withdrawn from the bottom of the distillation column to maintain said temperature and pressure.

2. The process of claim 1 wherein the initial mixture further comprises tetrachloroethylene and HCl and wherein the HCl is removed as a top product of the distillation column and the tetrachloroethylene is removed as a bottom product of the distillation column.

3. The process of claim 1 wherein said initial mixture further comprises hydrogen chloride, tetrachloroethylene and minor amounts of other halogenated products present in an effluent mixture from the preparation of 2,2-dichloro-1,1,1-trifluoroethane and 2-chloro-1,1,1,2- tetrafluoroethane by the reaction of tetrachloroethylene with excess hydrogen fluoride.

4. The process of claim 1 wherein the temperature is from 125° C. to 210° C.

5. The process of claim 1 wherein the pressure of the column is from 1.5 MPa to 2.5 MPa.

6. The process of claim 1 wherein the at least one low-boiling azeotrope is the azeotropes of the HF and both 2,2-dichloro-1,1,1-trifluoroethane and 2-chloro-1,1,1,2-tetrafluoroethane.

* * * * *